US 6,680,399 B2

(12) United States Patent
Anderson et al.

(10) Patent No.: US 6,680,399 B2
(45) Date of Patent: *Jan. 20, 2004

(54) PROCESS FOR THE MANUFACTURE OF ALKOXYSILANES AND ALKOXY ORTHOSILICATES

(75) Inventors: Amos R. Anderson, Adrian, MI (US); Jeffrey G. Meyer, Adrian, MI (US)

(73) Assignee: AK Research Company, Adrian, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 10/328,436

(22) Filed: Dec. 23, 2002

(65) Prior Publication Data

US 2003/0229241 A1 Dec. 11, 2003

Related U.S. Application Data

(63) Continuation of application No. 10/163,839, filed on Jun. 6, 2002, now Pat. No. 6,580,000.

(51) Int. Cl.$^7$ .................................................. C07F 7/18
(52) U.S. Cl. ....................................................... 556/470
(58) Field of Search ......................................... 556/470

(56) References Cited

U.S. PATENT DOCUMENTS

| | | | |
|---|---|---|---|
| 4,487,949 A | 12/1984 | Mallon | 556/470 |
| 4,727,173 A | 2/1988 | Mendicino | 556/470 |
| 4,761,492 A | 8/1988 | Childress et al. | 556/482 |
| 4,762,939 A | 8/1988 | Mendicino | 556/470 |
| 4,778,910 A | 10/1988 | Stoffer et al. | 556/470 |
| 4,931,578 A | 6/1990 | Ohta et al. | 556/470 |
| 4,999,446 A | 3/1991 | Moody et al. | 556/470 |
| 5,084,590 A | 1/1992 | Ritscher et al. | 556/470 |
| 5,103,034 A | 4/1992 | Cho et al. | 556/470 |
| 5,728,858 A | 3/1998 | Lewis et al. | 556/470 |
| 6,166,237 A | 12/2000 | Simandan et al. | 556/470 |
| 2002/0188146 A1 | 12/2002 | Steding et al. | 556/472 |

FOREIGN PATENT DOCUMENTS

| | | |
|---|---|---|
| DE | 196 19 161 | 11/1997 |
| DE | 100 48 160 | 5/2001 |
| EP | 0 182 814 | 1/1991 |
| EP | 0 311 861 | 2/1993 |
| EP | 0 456 754 | 12/1993 |
| EP | 0 529 804 | 4/1996 |
| EP | 0 785 180 | 7/1997 |
| EP | 0 517 398 | 9/1997 |
| EP | 0 835 877 | 4/1998 |
| EP | 0 657 214 | 3/1999 |
| EP | 0 931 587 | 7/1999 |
| EP | 0 947 521 | 10/1999 |
| EP | 1 000 658 | 5/2000 |
| EP | 0 709 388 | 4/2001 |
| EP | 1 093 851 | 4/2001 |
| EP | 0 748 255 | 5/2001 |
| EP | 1 157 993 | 11/2001 |
| EP | 1 172 366 | 1/2002 |
| FR | 91 07463 | 6/1991 |
| GB | 2 121 310 | 12/1983 |
| GB | 2 179 041 | 3/1990 |
| GB | 2 223 018 | 7/1990 |
| GB | 2 263 113 | 3/1996 |
| GB | 2 277 518 | 7/1997 |
| GB | 2 294 933 | 9/1998 |
| WO | 90/08589 | 8/1990 |
| WO | 90/09239 | 8/1990 |
| WO | 91/16328 | 10/1991 |
| WO | 92/14547 | 9/1992 |
| WO | 97/00131 | 1/1997 |
| WO | 97/34694 | 9/1997 |
| WO | 98/26866 | 6/1998 |
| WO | 99/32224 | 7/1999 |
| WO | 99/34918 | 7/1999 |
| WO | 99/44974 | 9/1999 |
| WO | 99/51340 | 10/1999 |
| WO | 01/16063 | 3/2001 |
| WO | 01/17673 | 3/2001 |
| WO | 01/47937 | 7/2001 |

OTHER PUBLICATIONS

Journal of Catalysis 145, 53–543 (1994); "Reaction Pathway of Formation of Methoxysilanes in the Reaction of Silicon with Methanol Catalyzed by Copper(I) Chloride"; Masaki Okamoto, et al.

*Primary Examiner*—Samuel Barts
(74) *Attorney, Agent, or Firm*—Nields & Lemack

(57) ABSTRACT

Process for the production of alkoxysilanes of the formula HSi(OR)$_3$, where R is an alkyl group containing 1 to 6 carbon atoms, and/or alkyl orthosilicates of the formula Si(OR)$_4$, where R is an alkyl group containing 1 to 6 carbon atoms. In a preferred embodiment, the process comprises reacting silicon metal with an alcohol in a suitable solvent in the presence of a cupric bis(diorganophosphate) catalyst. A polymeric form of ethyl orthosilicate, a by-product of the reaction, is the preferred solvent. The production of triethoxysilane and tetraethyl orthosilicate is preferred, with triethoxysilane being particularly preferred.

12 Claims, No Drawings

PROCESS FOR THE MANUFACTURE OF ALKOXYSILANES AND ALKOXY ORTHOSILICATES

This application is a Continuation of U.S. patent application Ser. No. 10/163,839 filed on Jun. 6, 2002, now U.S. Pat. No. 6,580,000 the disclosure of which is hereby incorporated by reference.

BACKGROUND OF THE INVENTION

The present invention is directed to the production of alkoxysilanes and alkoxy orthosilicates by reacting silicon metal with alcohols in the presence of a suitable catalyst.

Alkoxysilanes are useful chemicals for the synthesis of organosilanes used as silane-coupling reagents. Trimethoxysilane ($HSi(OCH_3)_33$), for example, can be synthesized directly by reaction of silicon metal with methanol in the presence of copper(I) chloride as a catalyst. Pioneering work by E. Rochow built the direct reaction of silicon with alkyl chlorides into the silicone industry. Rochow discovered that a mixture of elemental copper in silicon provided optimum conditions for reactions in gas fluidized reactors. Later work by the Japanese involved liquid phase reactions using copper chloride catalyst in an aromatic solvent at high temperatures.

Depending upon the reaction conditions, pretreatment conditions, and the particular catalyst chosen, the yield of the desired trialkoxysilane can vary widely. Tetraalkyl orthosilicate is a common by-product (and also a valuable by-product with sufficient commercial value), formed either directly from the reaction of elemental silicon and alcohol, or from the secondary reaction of trialkoxysilane and alcohol. Depending upon the identity of the particular alcohol used in the reaction, alcohol reduction, dehydration and/or dehydrogenation side reactions also may be problematic. Where triethoxysilane is the desired end-product, thermal degradation of the ethanol reactant can lead to olefins and their incorporation into the silane reaction.

U.S. Pat. No. 5,728,858 discloses a direct process for producing trialkoxysilanes in which silicon metal is slurried in a thermally stable solvent in the presence of a halogen-free catalyst precursor. The catalyst precursor includes copper, at least a part of which is not in the copper(0) state and is reducible to the copper(0) state. The copper(0) is then fully reduced to generate a catalyst for the reaction of the silicon metal with an alcohol, and the reaction is carried out. Suitable thermally stable solvents disclosed include polyaromatic and alkylated aromatic compounds. However, previous documents claim aromatics are critical but do not clearly describe chemistry of their role in their process. Using simpler chemical structures can avoid problems in process improvement, control and environmental management.

It therefore would be desirable to provide a process for the production of alkoxysilanes and or alkyl orthosilicates from silicon metal and alcohol in high yield that does not suffer from the drawbacks of the prior art.

It further would be desirable to provide a process for the production of alkoxysilanes and/or alkyl orthosilicates from silicon metal and alcohol that eliminates the pre-reduction of copper to form the catalyst.

It further would be desirable to provide a process for the production of alkoxysilanes and/or alkyl orthosilicates using a liquid phase reaction without an exotic solvent and into which a catalyst could be introduced in order to control the reaction rate.

It still further would be desirable to provide an improved catalyst for the reaction of silicon metal with alcohol to produce alkoxysilanes and/or alkyl orthosilicates in high yield.

Other objects and advantages of the present invention will be made apparent by the following description and examples.

SUMMARY OF THE INVENTION

The problems of the prior art have been overcome by the present invention, which provides a process for the production of alkoxysilanes of the formula $HSi(OR)_3$, where R is an alkyl group containing 1 to 6 carbon atoms, and/or alkyl orthosilicates of the formula $Si(OR)_4$, where R is an alkyl group containing 1 to 6 carbon atoms. In a preferred embodiment, the process comprises a slurry reaction wherein silicon metal is reacted with an alcohol in a suitable solvent in the presence of a cupric bis(diorganophosphate) catalyst. A polymeric form of ethyl orthosilicate, a by-product of the reaction, is the preferred solvent. The production of triethoxysilane and tetraethyl orthosilicate is preferred, with triethoxysilane being particularly preferred. Auxiliary reduction with hydrogen or other reducing agents is not required. Judicious addition of catalyst and solvent during the reaction can sustain reaction rate and selectivity.

DETAILED DESCRIPTION OF THE INVENTION

The process of the present invention is based upon the following chemical reactions:

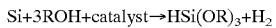

$$Si+3ROH+catalyst \rightarrow HSi(OR)_3+H_2$$

wherein R is an alkyl group of 1 to 6 carbon atoms, preferably 1 to 2 carbon atoms, most preferably 2 carbon atoms. The major by-product of this reaction forms the tetraalkyl orthosilicate:

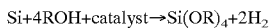

$$Si+4ROH+catalyst \rightarrow Si(OR)_4+2H_2$$

In addition, the trialkoxysilane can further react in the presence of sodium hydroxide as follows:

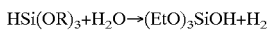

$$HSi(OR)_3+H_2O \rightarrow (EtO)_3SiOH+H_2$$

The process conditions and catalyst of the present invention favor the production of trialkoxysilane.

In accordance with the present invention, the liquid reaction medium is an organosilicate, preferably alkyl orthosilicate or alkyl orthosilicate polymer. Most preferably the alkyl group is ethyl. Advantageously, alkyl silicate or derivatives thereof are by-products of the reaction to trialkoxysilane. Suitable derivatives are of the formula $Et(OSi(OEt)_2)_nOEt$, where n is from 1 to 10, preferably 2 to 5. The most preferred medium is a condensation polymer of tetraethyl orthosilicate corresponding analytically to the pentamer as discussed in further detail below. Tetraethyl orthosilicate itself also can be used. The reaction medium can periodically cleaned such as by extraction and distillation.

More specifically, the basic composition unit of the solvent is tetraethyl orthosilicate or TEOS ($(EtO)_4Si$) commercially known as "Ethyl Silicate Pure" when distilled, or "Ethyl Silicate Condensed" when obtained without further purification from the manufacturing process. This composition contains 28% $SiO_2$. Ethyl Silicate-40 or "ES-40" is the major commercial form of ethyl silicate, and contains 40% $SiO_2$. It is easily made from "ethyl Silicate Condensed" by adding water and a small amount of hydrochloric acid, then distilling the appropriate amount of ethanol. This reaction not only forms dimers and trimers, but a complex permutation of structures in three dimensions. Data demonstrate that the dimer boils at 235°, whereas the "monomer" TEOS boils at 170° C. Higher molecular weight polymers of TEOS boil above 250°. Thus, the dimer and higher "condensation polymers" of TEOS are well suited for the instant process since they will not boil off with the products TES and TEOS.

By $SiO_2$ content, ES-40 is calculated to average 5 units of monomer, but by analysis commercial ES-40 contains about 25% TEOS. The remaining 75% is polymer ranging from dimer to diverse three dimensional structures containing up to a dozen TEOS units. The less volatile portion of ES-40 ideally remains in the reactor and provides a suitable medium for reacting silicon with ethanol in the presence of catalyst.

The higher molecular weight polymers of TEOS can gel upon prolonged heating and reaction with impurities (especially water) in reactants. ES-40 holds up without significant gelation when held below 220° C. for 24 hours, which is sufficient to process a charge of silicon, after which the solvent medium can be re-worked by removing un-reacted silicon and less soluble components formed in the reaction medium. The re-worked medium then can be recycled to the next batch.

Thus the reaction medium can be the dimer, the trimer, higher polymeric organosilicates formed by the reaction of TEOS and TES by water and heating, or mixtures thereof.

The elemental silicon used as a reactant in the process of the present invention is not particularly limited. Suitable sources include commercially available grades of silicon, in particulate or powder form. Purities of commercial grade silicon are in the range of about 80% to about 99% by weight, with particle sized from about 50 to about 100 5 $\mu$m. Dry milling silicon along with the catalyst, such as with a vibrating mill or preferably a ball mill, can improve the reaction and is preferred. The amount of silicon used is a function of the amount of solvent. Preferably the amount of silicon used is in a weight ratio of about 1:5 to 2:1 to the amount of solvent.

Suitable alcohols useful as a raw material in the process of the present invention include alkyl alcohols, preferably those having 1 to 6 carbon atoms, more preferably 1 to 2 carbon atoms. Those skilled in the art will appreciate that the particular alcohol chosen, and more specifically, the particular alkyl alcohol chosen, will depend in part on the desired final product. Exemplary alcohols include methyl alcohol, ethyl alcohol, n-propyl alcohol, iso-propyl alcohol, n-butyl alcohol, iso-butyl alcohol, amyl alcohol, mixtures thereof, etc. Methyl and ethyl alcohol are particularly preferred, with ethyl alcohol being most preferred.

The preferred catalyst in accordance with the present invention is a metal organophosphate soluble in the reaction medium and demonstrating sufficient activity at relatively low temperatures. Maintaining the reaction temperature as low as possible reduces or eliminates difficulties associated with thermal dehydration of ethanol, which deleteriously can lead to the formation of olefins and their incorporation into the silane reaction. Olefin formation is generally undesirable due to the difficulty in separating carbosilanes produced by reaction of olefins with silicon from the desired product (e.g., ethyl triethoxysilane formed by reaction of ethylene with silane intermediate). The amount of catalyst used is an amount effective to catalyze the reaction. Generally an effective amount ranges from about 0.1 to about 0.5 parts by weight catalyst per part by weight of the silicon. Those skilled in the art will appreciate that the catalyst:silicon ratio leading to the most efficient reaction depends in part on the surface area of the silicon, with most finely divided silicon accommodating more catalyst.

Most preferably the catalyst is the copper salt of diethylphosphoric acid, $Cu((O)P(OEt)_2)_2$. This catalyst has been found to exhibit excellent solubility in the reaction medium and in the alcohol raw material, leave residues compatible with triethylsilicate chemistry, and have a unique ability to interact with silicon surfaces. The solubility of the catalyst in the reaction medium is particularly surprising, in view of the known fact that ionic salts and soaps are sparingly soluble in non-ionic solvents and in orthosilicates. The solubility of the catalyst in alcohol, particularly in ethanol, allows the catalyst to be added with feed if desired. Catalyst also can be added by ball milling with silicon or by direct addition, for example. Ball milling with silicon ensures contact between the catalyst and the silicon before reaction with ethanol, which can be advantageous. Contact during reaction with ethanol also can be advantageous.

The cupric bis(diethyl phosphate) can be prepared by several methods apparent to those skilled in the art. The procedure described by C. M. Mikulski et al. published in Z. Anorg. Allg. Chem. 1974, 403(2), 200–210, the disclosure of which is hereby incorporated by reference, is suitable for preparing the catalyst. That procedure heat cupric chloride with triethyl phosphate. The reaction displaced chloride while forming the diethylphospate needed to build the desired compound.

Other copper catalysts effective for catalyzing the reaction and that have appreciable solubility in the orthosilicate solvent (about 1% or more by weight of compound in the solvent) are within the scope of the present invention. Salts containing polymeric ether in their structure, and other organophosphates containing haloalkyl groups, such as cupric bis(2-chloroethyl)phosphate, are examples.

Suitable reaction temperatures are between about 120° C. and about 250° C., more preferably between about 150° C. and about 220° C., most preferably between about 160° C. and about 200° C. Suitable reaction pressures are from about 0.1 to 10 atmospheres, preferably from about 0.5 to 1 atmosphere. Reaction in a conventional stirred tank reactor has been found to be suitable, thereby utilizing conventional equipment and minimizing capital expense for specially designed equipment. Positioning the point of feed of the alcohol to encourage multi-point sparging of alcohol into the reactor is preferred. Removal of significant heat of reaction in larger reactors can be accomplished by pumping the reaction slurry through an external heat exchanger. Silicon can be added with catalyst to make-up silicon used up by the reaction. Preferably the reaction conditions and solvent:silicon ratio are maintained constant throughout the reaction to enhance reactivity and selectivity. Localized concentration and holdup of alcohol should be avoided by utilizing rapid mixing and by eliminating pockets were alcohol can accumulate.

The order of addition of reactants is not particularly limited. For example, the alcohol can be added to a slurry of fine silicon metal suspended in ethyl orthosilicate oligomer with the catalyst. The solubility of the catalyst in the solvent allows the catalyst to be added with the feed. Additional catalyst can be added during the reaction to increase the reaction rate or to control the reaction. Alternatively, the catalyst can be milled with the silicon or can be added directly to the reaction.

If activation of silicon is desired, the medium can be tetraethyl orthosilicate or an ethyl orthosilicate oligomer. Activation of silicon can be carried out simply by heating catalyst with silicon in the medium prior to alcohol addition. It is believed that the activation process occurs spontaneously while addint alcohol to the silicon slurry in the organosilicate solvent, and is essentially complete while waiting an hour or two after the reation has attained 150° C. or higher.

Trialkoxysilane product should be removed from the reaction vessel as quickly as possible. If removal results in significant depletion of solvent, fresh solvent can be added back to the reactor. Since the solvent is a reaction by-product, additional solvent also can be added by partially condensing the solvent from reaction vapor with a distillation column. Depletion of solvent can be minimized by operating at lower temperature or by using higher boiling fractions of the solvent.

Partial condensation can carry undesirable amounts of triethoxysilane back into the reaction, where triethoxysilane can over-react to tetraethoxy orthosilicate, or can disturb the catalytic process. This can be avoided by stripping triethoxysilane from the orthosilicate before recycle.

The following examples are for illustration and are not to be construed as limitations on the present invention.

Unless otherwise indicated, the following standard procedure was used.

Into a 500 ml. spherical flask with three necks fitted with an electric heating mantle whose heat output is controlled by a transformer and a mechanical stirrer whose speed is maintained to suspend the silicon, is charged with 20 g standard silicon powder (200 mesh, 98+% purity dry powder) and 100 g organosilicate fluid (TEOS or ES-40). Catalyst is added to the slurry.

One neck of the flask is attached to a water cooled condenser whose inlet drains into a trap with a stopcock outlet. Thermometers are inserted into the flask and below the condenser to measure slurry and vapor temperatures. The system is sealed to vent by-product hydrogen gas only through the condenser outlet.

The slurry is pre-heated to a target temperature range and held for a determined interval (usually 1 hour above 160° C.), then ethanol (below 10 ppm water) addition is started beneath the surface of the slurry and m maintained at a standard rate (about 20 cc/hr). The temperature profile is maintained by adjusting the mantle voltage. Condensate is collected in the trap and removed at specific time intervals for weighing and analysis.

| Day | Operation (Hr-min) | Temperature (deg-C.) | EtOH Added grams | Condensate grams | TES g. | TEOS g. |
|---|---|---|---|---|---|---|
| 0 | 2-00 | 180–200 | 0 | 12.5 | .02 | na |
| 1 | 4-06 | 170–184 | 564.7 | 750.8 | 207.3 | 133.0 |
| 2 | 4-04 | 160–182 | 472.4 | 549.9 | 120.7 | 115.0 |
| 3 | 4-02 | 170–211 | 588.7 | 693.5 | 255.9 | 46.7 |
| 4 | 4-30 | 186–205 | 579.8 | 646.6 | 183.4 | 60.0 |
| (NOTE. After run added 2.0 g. CuDEP and 100 g. ES-40 to reactor) | | | | | | |
| 5 | 4-47 | 180–218 | 663.6 | 769.3 | 251.7 | 69.0 |
| (NOTE. Started using EtOH denatured with 5% TEOS) | | | | | | |
| (NOTE. After run added 50 g. ES-40 to reaction) | | | | | | |
| 6 | 4-11 | 207–224 | 540.9 | 628.3 | 172.4 | 55.4 |
| (NOTE Added 2 g. 10% Cu-DEP during mid-run) | | | | | | |

Each of 48 fractions of crude TES were analyzed by collecting $H_2$ liberated by hydrolysis in sodium hydroxide. Assays ranged 20% and below up to 48% TES.

A 5 liter still with column packed with Goodloe was initially charged with weak cuts, and these were stripped of EtOH (Cut 1). Strong cuts were charged and the distillation continued. A total of about 1000 g TES was in the crudes charged to the still. Forecut EtOH contained 8–13% TES, indicating that the Goodloe packing was not efficient. After recovering 467 g TES, the column was replaced by a 20" of Pro-Pak (fine stainless steel screen cylinders) and 145 g more high purity TES was recovered.

After removing a post cut, the column was removed and a flash vacuum distillation was set up. TEOS was stripped under full pump vacuum (about 10 mm Hg) with pot temperature of 109–153° C.

| Cut | 1 | 2 | 3 | 4 | 5 | 6* | 7 | 8 | vac | Resid |
|---|---|---|---|---|---|---|---|---|---|---|
| Head, C | 78.5 | 78.8 | 120 | 130 | 140 | 135 | 150 | 167.5 | 108–130 | |
| Pot, C. | 135 | 85 | 157 | 158 | 173 | 180 | 185 | 186 | 109–153 | |
| Wt | 962 | 729 | 390 | 9 | 467 | 145 | 47 | 42 | 750 | 375 |
| % TES | 7.7 | 12.2 | 13.2 | (90) | 90 | 98+ | (90) | 22.1 | 7.2 | 17.1 |

Samples of distillate are analyzed for triethyl silane (TES) by measurement of hydrogen released by hydrolysis. Hydrogen evolutoin is also measured during the specific time intervals. Net hydrogen volume difference between amount evolved and amount produced by TES reaction is used to calculate the amount of TEOS produced during the interval.

EXAMPLE 1

400 g of 200 mesh screened silicon, 800 g ES-40 and 8 g cupric bis(diethylphosphate) (CuDEP) were charged into a 2 liter 3-neck spherical flash, and were stirred and heated over 2 hours to 200° C. without adding ethanol. During the first day of operation, the temperature was kept below 180° C. Reaction temperature was increased during the 6 days of operation:

Within 10 g, the amount of TES in the fractions checked with the amount of TES charged. It should be noted that about 200 g TES analyzed in the crude cuts from the reaction was lost while standing over one week before distillation.

Increasing reaction temperature from the target 190° to 210° C. doubled the TES production rate and appeared to improve selectivity to the about 4–5:1 TES:TEOS during Days 3 and 5. Adding catalyst and ES-40 at the end of Day 4 appears to have improved performance during Day 5. Adding catalyst in the form of 10% CuDEP in EtOH appears to improve the reaction during Day 6, but not as remarkably as the Day 4 addition where 10 times the catalyst in solid form was added with ES-40 and the reaction was allowed to rest.

EXAMPLE 2

This experiment was conducted to demonstrate the effect of using less catalyst initially and attempting to make up the difference later in the reaction.

400 g of 200 mesh silicon metal, 807 g ES-40 and 4.0 g CuDEP catalyst were charged into a 2 liter 3 neck spherical flask, and were stirred and heated for 2 hours to 205° C. before adding EtOH. During the first day of operation, heating and EtOH feed rate were kept constant as pot temperature rose steadily. After 2 hours, hydrogen evolution accompanied the formation of largely TEOS. Four hours into the reaction, TES began forming at a steady rate until shutdown. One hour prior to shutdown, TEOS rate fell as did hydrogen rate, while essentially TES became the exclusive product. After shutdown, 1 g of additional catalyst and 100 g make-up ES-40 were added to the pot.

During Day 2, hydrogen evolution resumed one hour into the EtOH addition. Temperature was allowed to increase as EtOH feed rate and heating were kept constant. Two hours into the reaction, TEOS rate fell while TES rate remained constant, but somewhat lower than at the end of Day 1. 1 g of additional catalyst in 10 g ES-40 was added to the pot. Hydrogen rate increased while both TEOS and TES rate increased. After an hour, TEOS rate fell to the previous value, but TES rate improved, although not as high as Day 1. At shutdown, 2 g of additional catalyst was added to the pot.

During Day 3, hydrogen evolution resumed one hour into the EtOH addition, forming mostly TEOS. About 3 hours into the day, the TES rate rose to the Day 1 level, while TEOS rate fell off. Temperature was held nearly constant below 200° C. for the four hours the reaction was continued.

| Day | Operation (Hr-min) | Temperature (deg-C.) | EtOH Added (grams) | Condensate (grams) | TES (g.) | TEOS (g.) |
|---|---|---|---|---|---|---|
| 1 | 8-00 | 205–218 | 744 | 922 | 93.6 | 75.5 |
| (NOTE: Added 1 g catalyst + 100 g. ES-40 at end of day) | | | | | | |
| 2 | 8-00 | 185–230 | 690 | 868 | 103.2 | 46.3 |
| (NOTE: Added 1 g. catalyst + 10 g ES-40 after 6 hours into day added 2 g. catalyst after end of day) | | | | | | |
| 3 | 4-00 | 180–190 | 345 | 409 | 59.5 | 84.7 |

Each of 22 fractions of crude TES were analyzed by collecting $H_2$ liberated by hydrolysis in sodium hydroxide. Assays ranged 10% and below up to 22% TES.

A 5 liter still with a 15 inch Vigreux column was charged with select fractions totaling 1186 g, containing 178 g TES. Head temperature held 78.1° C. for the first fraction, which weighed 160 g, which was analyzed to contain 5.2% TES.

The slurry of silicon in the reaction medium had the consistency of cold motor oil with no signs of gel. The entire contents of the spherical flask after the reaction period weighed 921 g. A sample of this slurry was extracted with ethanol and dried, indicating 320 g residual silicon (and catalyst residue) Ethanol extracts were colorless, with some grey silt. Clear liquid decanted from the residual slurry was slightly green. Upon standing in air several days, this liquid formed a hard gel. This hard gel turned noticeably blue in aqueous ammonia, indicating the presence of copper in the reaction medium.

| Material Balance Total inputs to the reaction were measured to be 3198 g: | |
|---|---|
| ES-40 charge | 917 g |
| Silicon powder | 400 g |
| Catalyst | 8 g |
| Ethanol feed | 1173 g |
| TEOS in EtOH feed | 100 g |

Total recoveries were measured and estimated to match the inputs:

| | |
|---|---|
| Condensate (measured) | 2199 g |
| Residue (measured) | 921 g |
| Hydrogen (by stoich.) | 6 g |
| EtOH loss in vent (estim.) | 22 g |
| Other losses | 50 g |

The 921 g residue reported above was estimated to contain 328 g un-reacted silicon. 500 g of dry solids from the slurry were dissolved in 10% NaOH, then the residue was extracted in concentrated HCl. Copper was not indicated in the acid extract by absence of blue color upon mixing with ammonia water, demonstrating that the catalyst is not being simply hydrolyzed into copper hydroxides.

Although significantly less than in Example 1, the production of TES demonstrated typical behavior: steady rate after initial surge of TEOS. Day 3 showed that pot temperature above 200° C. is not necessary to ensure good TES rate. Lower initial charge of catalyst than in Example 1 seems responsible for less TES, but eventually adding the amount used in Example 1 did not immediately lead to the high TES rate seen in Example 1.

EXAMPLE 3

This experiment used "condensed" TEOS in place of ES-40 as the solvent. Difficulties in maintaining reaction temperature were addressed by using a reflux head setup. Operating within the very narrow constraint imposed by the 170° C. boiling point of TEOS, a good TES rate was attained with 1:1 selectivity.

20 g of 200 mesh Si, 1 g CuDEP and 100 g "Condensed" ethyl silicate were pre-heated for 1 hour at 165–170° C. (b.p. TEOS=169° C.) in the usual 500 cc reaction flask, only replacing the total vapor takeoff with a reflux takeoff head. The condensate accumulating above the takeoff valve could be removed intermittently, but head temperature fell throughout the course of reaction from 140° C. to 80° C. EtOH feed rate was kept about 0.3 cc/min.

After 6 hours and 20 minutes at 170° C., 107.9 g of condensate containing 15.0 g TES and 17.2 g TEOS was produced.

About 50% of the silicon reacted after 15 hours. Material balance on the charge and residue indicated 34 g TEOS boiled off the charge into the product, resulting in EtOH free product containing about 1 part TES and 2 parts TEOS (one part of which was carry-over). The reaction slurry residue settled clear from the residue and had a light blue color.

Operating within the very narrow constraint imposed by the 170° C. boiling point of TEOS, a good rate was attained with 1:1 selectivity.

EXAMPLE 4

The experiment compares the CuDEP catalyst to conventional copper hydroxide catalyst.

The standard experiment reacting 20 g silicon in TEOS with ethanol was carried out in a 55 cc flask fitted with stirrer, mantle, pot and head thermometers and a Dean-Stark trap which collected all vapor condensate passing up a short glass column. The standard 1 g CuDEP was replaced with 0.3 g Griffin copper hydroxide (57.5% Cu) containing the same amount of Cu as the CuDEP. The mixture of silicon, ethyl silicate and catalyst was stirred and heated at 160° C. for 1 hour before adding ethanol at 14 cc/hour beneath the surface of the slurry.

Within one hour of the start of EtOH addition, hydrogen rate rose to 20 cc/min and this rate continued for three hours. After 4.5. hours at 150° C., 104 g condensate containing 1.3 g TES was produced. By calculation from hydrogen rate, about 50 g ethyl silicate was also formed.

After cooling overnight, the reaction was re-heated and EtOH continued at about 14 cc/hour. Hydrogen started at 5 cc/min and rose, fell and rose in the range of 3–18. cc/min. The final 2 hour reaction was carried out at 160° C. After six hours at 150–160° C., 134 g of condensate containing 1.5 g TES was produced. By calculation, about 14 g TEOS was produced.

Copper hydroxide activated in less than an hour without hydrogen and produced over 40 g TEOS during the 10 hour reaction. However, less than 3 g TES was generated. Data from this test (Run #44) are compared with a very similar run (Run #35) using CuDEP in the table below:

slowed and thickened during the fourth day, but remained fluid, enabling assay of residual silicon and workup of residue.

20 g of dry old 200 mesh silicon powder was roll milled with about 50 g ES-40 and 1 g CuDEP using steel balls for 9 hours. The ground slurry was transferred to the reactor and ES-40 was made up to usual amount (here 117 g). The mix was held at 170° C., then EtOH was fed at the rate of 37 cc/hr. Hydrogen rate increased slowly to 6 cc/min. over 2.5 hours, then rose quickly to 25 cc/min.

Reaction for 4.5 hours at 170° C. produced 156.1 g condensate containing 4.3 g TES and 4.9 g TEOS.

During Day 2, upon re-heating and initiation of EtOH feed, the hydrogen rate started above 40 cc/min. and over a period of 3 hours tapered down to about 20 cc/min. Injection of 1/3 g CuDEP in methanol immediately doubled the hydrogen rate for over 30 minutes.

Reaction for 5.5 hours at 170° C. produced 198 g condensate containing 35.1 g TES and 26.3 g TEOS.

During Day 3, the reaction started strong and tapered off while 2 g CuDEP in methanol, 1 g TES from previous cuts and 12 g ES-40 were injected with varying effectiveness.

Reaction for 5.5 hours at 170° C. produced 206.8 g condensate containing 9 g TES and 16.6 g TEOS.

During day 4, the run was terminated after 2 additional hours. Although the residue was thick, it was fluid and could be thinned with methanol. Reaction for 2 hours at 170° C. produced 57.4 g condensate containing 0.9 g TES and 3.6 g TEOS.

2 g of the 81 g tarry residue was thinned in methanol and mixed with 10% aqueous NaOH. The gases from the reac-

| | CuDEP Run #35 | | | | | | Cu(OH)2 Run #44 | | | | | |
|---|---|---|---|---|---|---|---|---|---|---|---|---|
| Time min. | Head Deg-C. | EtOH cc.fed | H2 liter | Dist gm.off | TES gm. produced | TEOS | Head Deg-C. | EtOH cc.fed | H2 liter | Dist gm.off | TES gm. produced | TEOS |
| 000 | 76  | 000 | 0.00 | 000 | 00.0 | 00.0 | 30  | 000 | 0.00 | 000 | 00.0 | 00.0 |
| 080 | 51  | 000 | 0.00 |     |      |      | 30  | 000 | 0.00 | 000 |      |      |
| 090 | 100 | 006 | 0.06 |     |      |      | 126 | 007 | 0.15 | 016 | 00.1 |      |
| 130 | 101 | 018 | 0.23 |     |      |      | 119 | 016 | 1.01 | 032 |      |      |
| 180 | 119 | 032 | 0.56 |     |      |      | 117 | 028 | 2.38 | 050 | 01.0 | 09.4 |
| 200 | 109 | 036 | 0.72 | 033 | 01.5 | 02.1 |     |     |      |     |      |      |
| 230 | 101 | 045 | 1.01 |     |      |      | 118 | 040 | 3.95 | 057 |      |      |
| 280 | 109 | 059 | 1.57 |     |      |      | 120 | 051 | 5.53 | 088 | 01.2 | 22.5 |
| 320 | 109 | 070 | 2.02 |     |      |      | 117 | 060 | 6.58 | 105 | 01.3 | 26.9 |
| 340 | 102 | 075 | 2.34 | 064 | 05.2 | 06.1 |     |     |      |     |      |      |

Both Runs cooled and settled overnight. Run was "started" when pct reached 150 deg-C.
NOTE: 50 g. TECS was added to Run #44, but not to Run #35.

| | CuDEP Run #35 | | | | | | Cu(OH)2 Run #44 | | | | | |
|---|---|---|---|---|---|---|---|---|---|---|---|---|
| 360 | 99  | 095 | 3.02 |     |      |      | 127 | 070 | 6.81  | 124 |      |      |
| 390 | 98  | 103 | 3.40 |     |      |      | 129 | 076 | 6.96  | 148 |      |      |
| 420 | 104 | 111 | 3.86 | 091 | 06.1 | 11.1 | 114 | 066 | 7.12  | 184 | 01.6 | 29.0 |
| 450 | 103 | 122 | 4.46 |     |      |      | 117 | 091 | 7.32  | 178 |      |      |
| 500 | 118 | 140 | 5.37 |     |      |      | 112 | 100 | 7.51  | 195 |      |      |
| 550 | 117 | 148 | 5.83 | 120 | 12.0 | 17.5 | 99  | 114 | 8.33  | 212 | 02.3 | 33.6 |
| 650 | 114 | 179 | 7.45 | 147 | 19.7 | 22.0 | 107 | 135 | 10.16 | 229 | 02.5 | 41.2 |
| 590 |     |     |      |     |      |      | 92  | 142 | 10.20 | 237 | 02.7 | 41.2 |

Copper hydroxide was much less productive and formed much more TEOS than TES, compared to CUDEP.

EXAMPLE 5

In this example, silicon was ball milled in ES-40 with CuDEP and was activated by ethanol at 170° C. over 2.5 hours. A small amount of methanol was added intentionally. The usual charge was made up and reaction temperature held at 170° C. At the end of the second day, shots of CuDEP in methanol were injected to boost reaction rate. The reaction tion with residual silicon (also Al) were collected, indicating 2.75 g silicon remained in the residue. This indicates an 85+% conversion of Si, of which 42% when to TES. The caustic residue formed a clear caustic upper layer and a heavy, viscous back layer of sodium silicate. Black iron powder precipitated from the lower layer after dilution with water.

Analysis of the first three cuts taken during Day 2 indicated 46.7% EtOH, 20.4% TES and 21% TEOS.

EXAMPLE 6

This experiment is a scale-up of the standard test, using 60 g silicon added to the standard charge. Over 4 days (21.5 hours operating time), 177.9 g TES and 139.0 g TEOS was formed. Over 80% of the silicon reacted. TEOS was injected on the second and third days to restore reaction rate. Concentration of TES attained 60% and selectivity TES/TEOS attained 3.0 or more.

EXAMPLE 7

The standard reaction was run except that half (0.5 g) of the same CuDEP catalyst was used. After 5 hours at 175–198° C., 121.8 g condensate containing 20.4 g TES and 29 g TEOS was produced.

During the second day, 2 cc TEOS was added when the hydrogen rate fell below 10 cc/min. 50 minutes later, the hydrogen rate increased to 40 cc/min. After 6.5 hours at 185–201° C., 152.5 g condensate containing 29.1 g TES and 25.7 g TEOS was produced.

During the third day, 2 cc TEOS was again added. About 1 hour later, the hydrogen rate rose from 10 to 30 cc/min. After 3.5 hours at 200–203° C., 83.2 g condensate containing 3 g TES and 19.5 g TEOS was produced.

With half the catalyst, 15 hours of reaction converted 94% of the silicon, with 45% forming TES.

What is claimed is:

1. A process for the production of alkoxysilanes, comprising:

milling a copper catalyst with elemental silicon;

reacting said mixture with an alcohol of the formula ROH wherein R is an alkyl group having 1 to 6 carbon atoms, in an orthosilicate solvent, wherein said copper catalyst is soluble in said solvent and is present in a catalytically effective amount.

2. The process of claim 1, further comprising heating said catalyst and silicon prior to reacting said mixture with said alcohol.

3. The process of claim 1, wherein said alkoxysilane comprises triethoxysilane.

4. The process of claim 1, wherein said alkoxysilane comprises tetraethyl orthosilicate.

5. The process of claim 1, wherein R is ethyl.

6. The process of claim 1, wherein said orthosilicate solvent is tetraethyl orthosilicate.

7. The process of claim 1, wherein said orthosilicate solvent is polymer of ethyl orthosilicate.

8. The process of claim 1, wherein said orthosilicate solvent comprises a polymeric organosilicate formed by the reaction of tetraethyl orthosilicate and triethyl silane.

9. The process of claim 1, wherein said catalyst is a copper salt of dialkylphosphoric acid.

10. The process of claim 1, wherein said copper catalyst is cupric bis(diethylphosphate).

11. The process of claim 1, wherein the reaction is carried out at a temperature from about 120° C. to about 250° C.

12. The process of claim 1, wherein said organic solvent is directly derived from the products of reaction of said silicon with said alcohol.

* * * * *